Nov. 25, 1969 D. L. ARMSTRONG Plant Pat. 2,944
PEACH TREE
Filed March 27, 1968
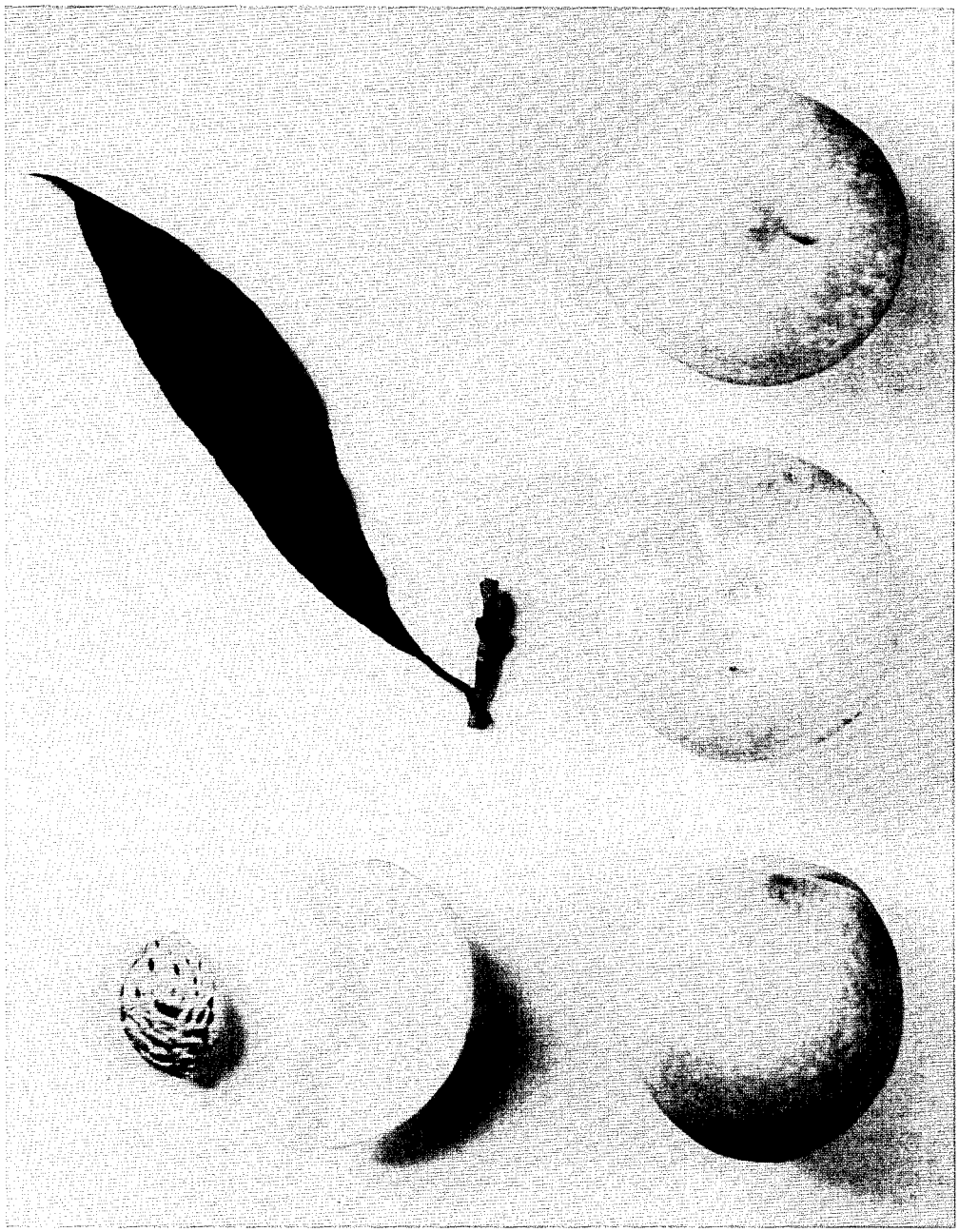
Inventor.
D. L. Armstrong
By: Robb & Robb
Attorneys.

United States Patent Office

Plant Pat. 2,944
Patented Nov. 25, 1969

2,944
PEACH TREE

David L. Armstrong, Ontario, Calif., assignor, by mesne assignments, to Stark Bro's Nurseries & Orchards Company, Louisiana, Mo., a corporation of Missouri Filed Mar. 27, 1968, Ser. No. 716,675
Int. Cl. A01h 5/08
U.S. Cl. Plt.—43 1 Claim The present invention relates to a new and distinct variety of peach tree of the yellow-fleshed, freestone fruit-bearing, dwarf tree type which was originated by me as an open-pollinated seedling of an unnamed and unpatented tall peach variety which itself was an unnamed and unpatented seedling derived from open-pollination of another tall peach variety whose pollen parent was the peach variety known as "Springtime" (Plant Patent No. 1,268), and whose seed parent was the result of several generations of breeding involving the peach varieties "Flamingo" (Plant Patent No. 661), "Rio Oso Gem" (Plant Patent No. 84), "Babcock" (unpatented), "Coolidge Double Pink" (unpatented), and "Swatow" (unpatented), the latter variety being a dwarf ornamental (sometimes referred to as "Chinese Dwarf" peach having large, many-petaled, light red flowers followed by soft-fleshed, clingstone fruit having a greenish-colored skin.

The new variety is one that resulted from an extensive breeding program conducted by me with the objective of producing improved, yellow-fleshed, freestone peach varieties having a dwarf tree habit and a succession of fruit ripening periods throughout the season for peach fruits. This new variety is one of the achievements of this objective, along with other desirable improvements, as evidenced by the following unique combination of characteristics which are outstanding in the new variety and which distinguish it from its parents, as well as from all other peach varieties of which I am aware:

(1) A vigorous, compact, bushy and dwarf tree habit with stem internodes averaging approximately ¼ inch in length and resulting in close spacing of the normal to large size leaves, giving a densely foliaged appearance to the tree which attains a height of 5 to 6 feet in about 10 years, with little or no pruning;
(2) A chilling requirement intermediate between "Springtime" peach (Plant Patent No. 1,268) and "Tejon" peach (unpatented);
(3) Showy, light pink, single flowers about 1½ inches in diameter;
(4) Heavy fruit crop production, as observed over a prolonged period of years at Wasco, Calif.
(5) Medium sized fruit of quite rounded appearance as grown at Wasco, Calif., and ripening in that area between June 16 and July 5, or about 2 weeks after the dwarf peach "Bonanza" (Plant Patent No. 2,213), said fruit having only a few flecks and streaks of red color in the flesh;
(6) Scant pubescence of medium length; and
(7) An attractive skin color which basically is Indian Yellow, attractively overlaid with splotches and streaks of red, particularly on one side of the fruit where it is substantially deeper in color because of the overlay, but with the skin color varying with the degree of coverage by the foliage.

The seed parent of this new variety was a yellow-fleshed, freestone peach of normal height, whose fruit ripens toward the latter part of June or early midseason, said fruit being of medium size, well-shaped and essentially round, with a little better than average skin color, and having a chilling requirement approximately equal to that of this new variety.

The new variety differs from the parent variety aforesaid pirmarily by having a dwarf tree habit as compared to the normal or tall tree habit of the parent.

The new variety differs from all of its ancestral varieties except "Swatow" in that it is dwarf in habit, while they are generally referred to as being tall in habit.

As compared with the "Swatow" peach, the new variety bears fruit which has a more attractive skin color, is much larger in size, with edible flesh, and is freestone instead of being clingstone like "Swatow" peach; the fruit of the new variety is much earlier ripening, and its flowers are the normal five petals, whereas the flowers of "Swatow" peach have thirty to forty petals.

In comparison with "Bonanza" dwarf peach, the new variety primarily differs by a ripening date which on the average is about two weeks later under growing conditions at Wasco, Calif.; its fruit is also normally ripe a few days after "Redhaven" peach (unpatented) in the same area; it has a lower chilling requirement; its fruit has somewhat shorter pubescence and is sufficiently distinct in this respect that it would normally be referred to as less fuzzy than "Bonanza" fruit; and the fruit also has substantially more skin color than "Bonanza" fruit under conditions existing at Wasco, Calif.

Asexual reproduction of my new variety by budding, as performed by me at Wasco, Calif., shows that the foregoing characteristics and distinctions come true to form and are established and transmitted through succeeding propagations.

The accompanying drawing shows typical specimens of the foliage, stem, fruit and stone of my new variety, with both exterior and sectional views of the fruit being shown, and all of said views being depicted in color as nearly true as is reasonably possible to make the same in a color illustration of this character.

The following is a detailed description of my new variety, as based upon observations of specimens grown at Wasco, Calif., with color terminology in accordance with Robert F. Wilson's Horticultural Colour Chart (hereinafter abbreviated as W) and Ridgway's Color Standards and Nomenclature (hereinafter abbreviated as R), except where general color terms of ordinary dictionary significance are obvious:

*Tree*

Habit: Vigorous; upright-spreading; compact; bushy; dwarf; stem internodes average approximately ¼ inch in length; leaves are of a relatively normal size and appearance for peaches.

Chilling requirement: Less than that for "Springtime" peach and slightly higher than that for "Tejon" peach.

Fruit production: Bears heavy crops under California conditions.

Current growth:

*Surface texture.*—Smooth at first, with small and minute lenticels; with age, some larger, cracked, slightly raised lenticels appear toward the base of the more vigorous shoots.

*Color.*—Green at first, or reddish on exposed surfaces, with lenticels appearing as small, near white dots, all becoming more brown with age.

Two-year wood:

*Surface texture.*—Somewhat bumpy and rough effect from raised nodes and buds and their closeness together on the stem; otherwise internodes generally smooth, with some slightly raised lenticels and irregular, longitudinal striations.

*Color.*—Brown, but sometimes reddish-brown.

Old wood:

*Surface texture.*—With increasing diameter of the stem, the bumpiness and rough effect from the nodes and buds becomes less as they are covered by the growth of the stem, becoming more smooth overall, with moderate number of raised lenticels and some small longitudinal fissures.

*Color.*—From grey to greyish-brown or reddish-brown on more exposed surfaces.

Leaves:

*Size.*—From 5½ inches to 6½ inches long; from 1¼ inches to 1½ inches wide.

*Shape.*—Lanceolate, with apex acuminate.

*Color (mature).*—Upper surface—Near Forest Green, Plate XVII (R). Under surface.—Near Chromium Green, Plate XXXII (R).

*Petiole.*—Medium length, medium thickness.

*Margin.*—Finely serrate; glandular.

*Glands.*—Mixed; usually reniform; some globose; medium size; usually 3 or 4, but sometimes 5 or 6 in number; borne both on the petiole and on the base of the blade.

Vegetative buds:

*Size.*—Small.

*Shape.*—Ovoid, unless compressed between flower buds.

*Scales.*—Thick pubescence of moderate length.

*Color.*—Dark brown.

*Flowers*

Dates first and full bloom: Over an eight-year period of observation at Wasco, Calif., first bloom varied from February 6 to March 5, and full bloom varied from February 26 to March 14.

Dormant flower buds:

*Shape.*—Ovoid.

*Scales.*—Pubescent.

*Color.*—Dark brown, with pubescence giving a whitish effect.

*Size (when fully open)*: Showy; medium size; about 1½ inches in diameter.

Petalage: Single; usually 5 petals.

Form (open flower): Cupped.

Color (open flower): Light pink.

*Fruit*

Ripening dates: Generally ripens about the fourth week in June at Wasco, Calif.; over an eight year period of observation, first ripening ranged from June 16 to July 5; usually ripens about 2 weeks after "Bonanza" dwarf peach, and about at the same time or a few days after "Redhaven" peach as grown at Wasco, Calif.

Maturity when described: Tree-ripe.

Size: Generally medium size.

*Axial diameter.*—From 2¼ inches to 2⅝ inches.

*Transverse diameter in suture plane.*—From 2⅜ inches to 2¾ inches.

*Transverse diameter at right angles to suture plane.*—From 2¼ inches to 2½ inches.

Form: Somewhat variable; nearly globose; usually slightly compressed laterally.

Suture: Usually shallow; extending from base to apex on the ventral side only; slight depression beyond pistil point.

Ventral surface: Rounded; sometimes slightly lipped; lips when present usually slightly unequal.

Stem cavity: Rounded; slightly elongated in suture plane, with suture showing strongly on one side and sometimes on both sides.

*Depth.*—From about ¼ inch to ⅜ inch.

*Width.*—From ⅝ inch to ⅞ inch.

Base: From rounded to truncate.

Apex: Rounded; pistil point usually very short and often insignificant.

Stem: From medium to heavy caliper; glabrous; weak adherence to stone.

*Length.*—From about ¼ to ⅜ inch.

Skin:

*Thickness.*—Medium.

*Texture.*—Medium.

*Tenacity to flesh.*—Free.

*Pubescence.*—From moderate to scant amount; medium length.

*Color.*—Ground color varies from near Straw-Yellow, Plate 604/1, page 67 (W) to near Chinese Yellow, Plate 606/1, page 68 (W), all heavily overlaid with mottling, streaks, flecks and blushes from near Jasper Red, Plate 018/1, page 107 (W) to near Oxblood Red, Plate 00823/3, page 191 (W).

Flesh:

*Quality.*—Medium firm; melting; fine; tender fibres.

*Aroma.*—Pronounced.

*Flavor.*—Good peach flavor; subacid; good balance between sugar and acid.

*Color.*—From near Indian Yellow, Plate 6/3, page 6 (W) to near Indian Yellow, Plate 6/1, page 6 (W), with a few flecks and streaks of near Crimson, Plate 22/1, page 22 (W), and with surface of pit cavity near Buttercup Yellow, Plate 5/3, page 5 (W).

Stone:

*Tenacity of flesh.*—Basically free; some adherence to flesh, especially along edges, until the fruit is fully ripe.

*Size.*—Medium; from about 1¼ inches to 1⅝ inches long; from about ⅞ inch to 1 inch wide; from about ⅝ inch to ¾ inch thick.

*Form.*—Ovoid.

*Base.*—Oblique.

*Hilum.*—Oval.

*Apex.*—Acute.

*Sides.*—Slightly unequal; irregularly furrowed toward apex; pitted from base to above center; pits circular or elongated.

*Ventral edge.*—Medium thickness; without wing.

*Dorsal edge.*—Medium width; with shallow, narrow groove usually throughout; ridges on either side interrupted.

*Color.*—Between Light Pinkish-Cinnamon, Plate XXIX (R) and Pinkish-Cinnamon, Plate XXIX (R).

I Claim:

1. A new and distinct variety of peach tree of the yellow-fleshed, freestone, fruit-bearing, dwarf tree type, substantially as herein shown and described, characterized particularly as to novelty by the unique combination of a vigorous, compact, bushy and dwarf tree habit, with stem internodes averaging approximately ¼ inch in length and resulting in close spacing of the normal to large size leaves, giving a densely foliaged appearance to the tree which attains a height of 5 to 6 feet in about 10 years with little or no pruning, a chilling requirement intermediate between "Springtime" peach (Plant Patent No. 1,268) and "Tejon" peach (unpatented), showy, light pink, single flowers about 1½ inches in diameter, heavy fruit crop production, as observed over a prolonged period of years at Wasco, Calif., medium sized fruit of quite rounded appearance as grown at Wasco, Calif., and ripening in that area between June 16 and July 5, or about 2 weeks after the dwarf peach "Bonanza" (Plant Patent No. 2,213), said fruit having only a few flecks and streaks of red color in the flesh, scant pubescence of medium length, and an attractive skin color which basically is Indian Yellow, attractively overlaid with splotches and streaks of red, particularly on one side of the fruit where it is substantially deeper in color because of the overlay, but with the skin color varying with the degree of coverage by the foliage.

No references cited.

ROBERT E. BAGWILL, Primary Examiner